(12) United States Patent
Ragauskas et al.

(10) Patent No.: US 8,206,303 B2
(45) Date of Patent: Jun. 26, 2012

(54) APPARATUS AND METHOD FOR SIMULATING ARTERIAL BLOOD FLOW UNDER VARIOUS PRESSURE CONDITIONS

(75) Inventors: Arminas Ragauskas, Kaunas (LT); Gediminas Daubaris, Kaunas (LT); Rolandas Zakelis, Kaunas (LT); Eugene A. Saxon, Seattle, WA (US); Arne H. Voie, Seattle, WA (US); Mailee Hess, Seattle, WA (US); Marc McDaniel, Seattle, WA (US); Timothy Myers, Snohomish, WA (US)

(73) Assignee: UAB Vittamed (LT)

( * ) Notice: Subject to any disclaimer, the term of this patent is extended or adjusted under 35 U.S.C. 154(b) by 530 days.

(21) Appl. No.: 12/545,599

(22) Filed: Aug. 21, 2009

(65) Prior Publication Data

US 2011/0045451 A1 Feb. 24, 2011

(51) Int. Cl.
*A61B 8/04* (2006.01)
(52) U.S. Cl. ......... 600/454; 600/455; 600/485; 600/561
(58) Field of Classification Search .................. 600/454, 600/455, 485, 561
See application file for complete search history.

(56) References Cited

U.S. PATENT DOCUMENTS

| | | | | |
|---|---|---|---|---|
| 3,371,660 A | * | 3/1968 | Carlin | 600/452 |
| 3,453,998 A | * | 7/1969 | Giglio | 600/452 |
| 3,706,304 A | * | 12/1972 | Sisler | 600/489 |
| 3,903,871 A | * | 9/1975 | Chisum et al. | 600/489 |
| 3,948,248 A | * | 4/1976 | Zuckerman et al. | 600/457 |
| 4,157,718 A | * | 6/1979 | Baehr | 604/27 |
| 4,282,882 A | * | 8/1981 | Langham | 600/489 |
| 4,286,455 A | | 9/1981 | Ophir et al. | |
| 4,907,595 A | | 3/1990 | Strauss | |
| 4,909,783 A | * | 3/1990 | Morrison | 604/30 |
| 4,984,567 A | * | 1/1991 | Kageyama et al. | 600/438 |
| 5,040,540 A | * | 8/1991 | Sackner | 600/485 |
| 5,052,934 A | | 10/1991 | Carey et al. | |
| 5,341,808 A | | 8/1994 | Rickey et al. | |
| 5,560,242 A | | 10/1996 | Flax | |
| 5,656,763 A | | 8/1997 | Flax | |
| 5,789,240 A | * | 8/1998 | Abdulrazik | 435/284.1 |
| 5,951,477 A | | 9/1999 | Ragauskas et al. | |
| 6,027,454 A | * | 2/2000 | Low | 600/489 |
| 6,547,734 B2 | * | 4/2003 | Madsen et al. | 600/438 |
| 6,589,189 B2 | * | 7/2003 | Meyerson et al. | 600/561 |
| 6,595,923 B2 | | 7/2003 | Sjoblom | |
| 7,122,007 B2 | * | 10/2006 | Querfurth | 600/485 |
| 7,147,605 B2 | * | 12/2006 | Ragauskas | 600/561 |
| 8,137,110 B2 | * | 3/2012 | Sakezles | 434/267 |
| 2003/0186203 A1 | * | 10/2003 | Aboud | 434/262 |
| 2005/0049581 A1 | * | 3/2005 | Gerlach | 606/1 |
| 2006/0155164 A1 | * | 7/2006 | Clerin et al. | 600/36 |
| 2007/0054256 A1 | * | 3/2007 | Low et al. | 434/268 |
| 2007/0117077 A1 | * | 5/2007 | Gordon et al. | 434/262 |

\* cited by examiner

*Primary Examiner* — David Rogers
(74) *Attorney, Agent, or Firm* — St. Onge Steward Johnston & Reens LLC

(57) ABSTRACT

An apparatus and method for simulating human ophthalmic artery for testing of ultrasound devices is disclosed, whereby two chambers are provided and are capable of being independently pressurized, one representing the intra-cranial space and the other representing extra-cranial space, and whereby a tube running through both chambers is provided, simulating the course of the ophthalmic artery and capable of being pressurized to stimulate arterial pressure. The apparatus is operated by pressuring both chambers, and pumping a blood-imitating fluid through the vessel in a pulsatile manner.

26 Claims, 3 Drawing Sheets

APPARATUS AND METHOD FOR SIMULATING ARTERIAL BLOOD FLOW UNDER VARIOUS PRESSURE CONDITIONS

FIELD OF THE INVENTION

The present invention relates generally to the field of devices used for testing of ultrasonic imaging systems. More specifically, it is concerned with an apparatus and method for simulating arterial blood flow hemodynamics under various pressure conditions in the intra-cranial and extra-cranial segments of human ophthalmic artery to provide a suitable test environment for the multiple element ultrasound transducers and associated controlling hardware and software.

BACKGROUND OF THE INVENTION

Ultrasound devices are now well established as tools for a variety of medical diagnoses. One of the widely used clinical ultrasound imaging systems is Doppler processing system, which enables a user to make estimates of blood velocity in various vessels of a patient's body by extracting the Doppler shift from returned echo signals reflected off of blood cells. Doppler ultrasound techniques and apparatus thus offer a convenient and non-invasive means for diagnosing various conditions related to blood flow velocity in different parts of human body.

One of such conditions capable of being determined ultrasonically is the intracranial pressure. The measurement of intracranial pressure (ICP) is important in diagnosing and treating various pathophysiological conditions caused by head trauma, hemorrhage, tumors, inflammatory diseases and the like. A few methods and techniques have been proposed for non-invasive assessment of intracranial pressure. One such method is described in U.S. Pat. No. 5,951,477 to Ragauskas et al., which comprises steps of using an ultrasound Doppler device to detect the velocities of the blood flow inside the ophthalmic artery for both intra-cranial and extra-cranial ophthalmic artery portions and applying a small pressure to the eye of a patient, sufficient enough to equalize the blood flow measurements of the internal and external portions of the ophthalmic artery. The pressure at which such equalization occurs is found to be an acceptable indication of the intracranial pressure.

Although the above method of using the ultrasound equipment to measure the intracranial pressure has been in use for a number of years, there is still a need for test equipment which can simulate human arterial flow, permit detailed hemodynamic measurements, and allow clinical-type ultrasound examinations.

A number of attempts have been made in the past to provide effective diagnostic devices that mimic blood flows and systolic movement of vessels within the human body. One such device disclosed in U.S. Pat. No. 5,560,242, issued to Flax, comprises an open-cell foam material matrix having a first density and a movable belt having a second density. The belt rotates on pulleys to simulate blood flow. In another embodiment the belt is replaced by a rotating disk of the same material as the belt such that differing blood flow rates between adjacent blood vessels can be simulated for ultrasonic imaging. However, there are several disadvantages associated with this type of phantom device. One of such disadvantages is that the scattering signals reflected off the belt are too ideal and do not indicate how the ultrasound system will operate under more realistic conditions.

Another type of blood flow device utilizes blood mimicking fluid flow through tubes to simulate blood flow within the human body. The blood mimicking fluid contains a scatter material with reflects sonic waves similarly to the way blood platelets reflect ultrasonic waves in blood. For example, U.S. Pat. No. 6,595,923 to Sjoblom discloses one such device comprising a tissue-mimicking material containing a plurality of fluid flow path through which fluid is pumped. The fluid flow paths are made of tubing and each extends over a different portion of the depth of the device and at a different angle, thus simulating blood vessels located at various depths within the human body. One of the problems with such device is that it is incapable of producing a flow of blood mimicking fluid with a physiologically correct pressure and flow distribution data, as it only produces a flow of constant character and constant pressure.

U.S. Pat. No. 5,052,934, issued to Carey, et al., discloses a device for evaluation of prosthetic valves and cardiac ultrasound procedures, wherein a controlled pulsatile flow of a blood mimicking fluid is passed through a multi-chambered region into which are mounted mitral and aortic valves and adjustably positioned ultrasound transducers. Although such device is capable of producing a pulsatile flow, thus assuring a uniform distribution of scatter material in the blood mimicking fluid and providing more accurate flow rates over a wide range of flow velocities, because of its specific design it is clearly limited to clinical evaluation of cardiac ultrasound procedures and is not suitable for evaluation of ultrasound devices used to detect the velocities of the blood flow inside the human ophthalmic artery.

Therefore, none of the above-shown systems are able to produce flows of a blood simulating fluid that have characteristics equivalent to those of blood flow in the intra-cranial and extra-cranial segments of human ophthalmic artery.

SUMMARY OF THE INVENTION

Accordingly, it is an object of the present invention to provide an apparatus and method for simulating arterial blood flow hemodynamics in the intra-cranial and extra-cranial segments of human ophthalmic artery to provide a suitable test environment for ultrasound devices.

In order to overcome the deficiencies of the prior art and to achieve at least some of the objects and advantages listed, an apparatus for simulating arterial blood flow under various pressure conditions is provided, comprising a first chamber, a second chamber, a sealing plug between the two chambers, a tube extending through the sealing plug from the first chamber to the second chamber, at least two pressure loops connected to the first chamber and the second chamber for independent pressurizing of each said chamber, and a flow loop connected to the tube for controlling a fluid flow and pressure in the tube.

In some embodiments, the flow loop may comprise a flow reservoir, at least one constant-flow pump, at least one pulsatile-flow pump, and a pressure line.

The second chamber may be placed inside the first chamber, and may comprise a cavity that is conical in shape to define a shape and volume representative of an orbital cavity. In certain embodiments, the apparatus may further comprise an ultrasound transducer tightly fitted into the cavity thereby sealing said second chamber.

In some embodiments, the tube may comprise material designed to simulate an arterial wall.

Each of the two pressure loops may further comprise at least one pressure sensor and at least one water bag, and may be filled with water. The pressure sensor may further be connected to an ultrasound device.

In some embodiments, the constant-flow pump and the pulsatile-flow pump may be placed on an isolated surface to prevent transfer of mechanical vibrations. In other embodiments, tubing may be placed on an outflow side of the constant-flow pump and the pulsatile-flow pump to assist with absorption of mechanical vibration from the pumps and to shape a diastolic component of the pulsatile wave. In yet another embodiment, a pulse dampener may be placed on an outflow side of the constant-flow pump and the pulsatile-flow pump to assist with absorption of mechanical vibration from the pumps and to shape a diastolic component of the pulsatile wave. The constant-flow pump and the pulsatile-flow pump may further be connected in parallel.

In some embodiments, the pressure line may comprise a water bag and a pressure sensor. The water bag may be filled with a blood simulating fluid, and blood simulating fluid may be pumped through the flow loop in a pulsatile manner.

In certain embodiments, the sealing plug may comprise silicone.

In an additional embodiment, an apparatus for simulating arterial blood flow under various pressure conditions is provided comprising a first chamber, a second chamber placed inside the first chamber, a sealing plug between the two chambers, a tube extending through the sealing plug from the first chamber to the second chamber, and at least two pressure loops, one connected to the first chamber and the other connected to the second chamber for independent pressurizing of each chamber. The tube is connected to a flow loop comprising a flow reservoir, at least one constant-flow pump, at least one pulsatile-flow pump, and a pressure line for controlling a fluid flow and pressure in the tube. The pressure line further comprises a water bag and a pressure sensor. A blood simulating fluid is pumped through the flow loop in a pulsatile manner. The two pressure loops further comprise a water bag and a pressure sensor.

An embodiment of a method for simulating arterial blood flow under various pressure conditions is also provided. The method comprises the steps of pressurizing a first chamber using a first pressure loop, pressuring a second chamber using a second pressure loop, connecting the first chamber with the second chamber by a tube, connecting the tube to a flow loop, and pumping a fluid through the tube and the flow loop.

In some embodiments, the fluid may be a blood simulating fluid, and may be pumped through the tube and the flow loop in a pulsatile manner.

The method may further comprise the step of placing the second chamber inside the first chamber. In certain embodiments, the first chamber may be separated from the second chamber by inserting a sealing plug.

In certain embodiments, the pressure is created within the first pressure loop and the second pressure loop by filling the pressure loops with water. In some embodiments, the first pressure loop and the second pressure loop may comprise at least one water bag and at least one pressure sensor. The pressure sensor may further be connected to an ultrasound device.

The second chamber may comprise a conical cavity representative of an orbital space. In some embodiments, the method may further comprise the step of measuring a flow of the fluid in the tube by inserting an ultrasound transducer into the conical cavity.

In some embodiments, the flow loop is formed by connecting a flow reservoir to at least one constant-flow and at least one pulsatile-flow pump, connecting the constant-flow pump and the pulsatile-flow pump to a pressure line, and connecting the pressure line to the tube. The constant-flow pump and the pulsatile-flow pump may further be placed on isolated surface prevent a transfer of mechanical vibrations. The constant-flow pump and the pulsatile-flow pump may further be connected in parallel.

In certain embodiments, the pressure line comprises a water bag and a pressure sensor. The pressure sensor may further be connected to an ultrasound device.

Other objects of the invention and its particular features and advantages will become more apparent from consideration of the following drawings and accompanying detailed description.

DETAILED DESCRIPTION OF THE INVENTION

The present invention is designed to simulate the human ophthalmic artery running through both the brain and orbital spaces. The purpose of the device of the present invention is to provide a suitable testing environment for multiple element ultrasound transducer and associate controlling hardware and software.

Figure 1:
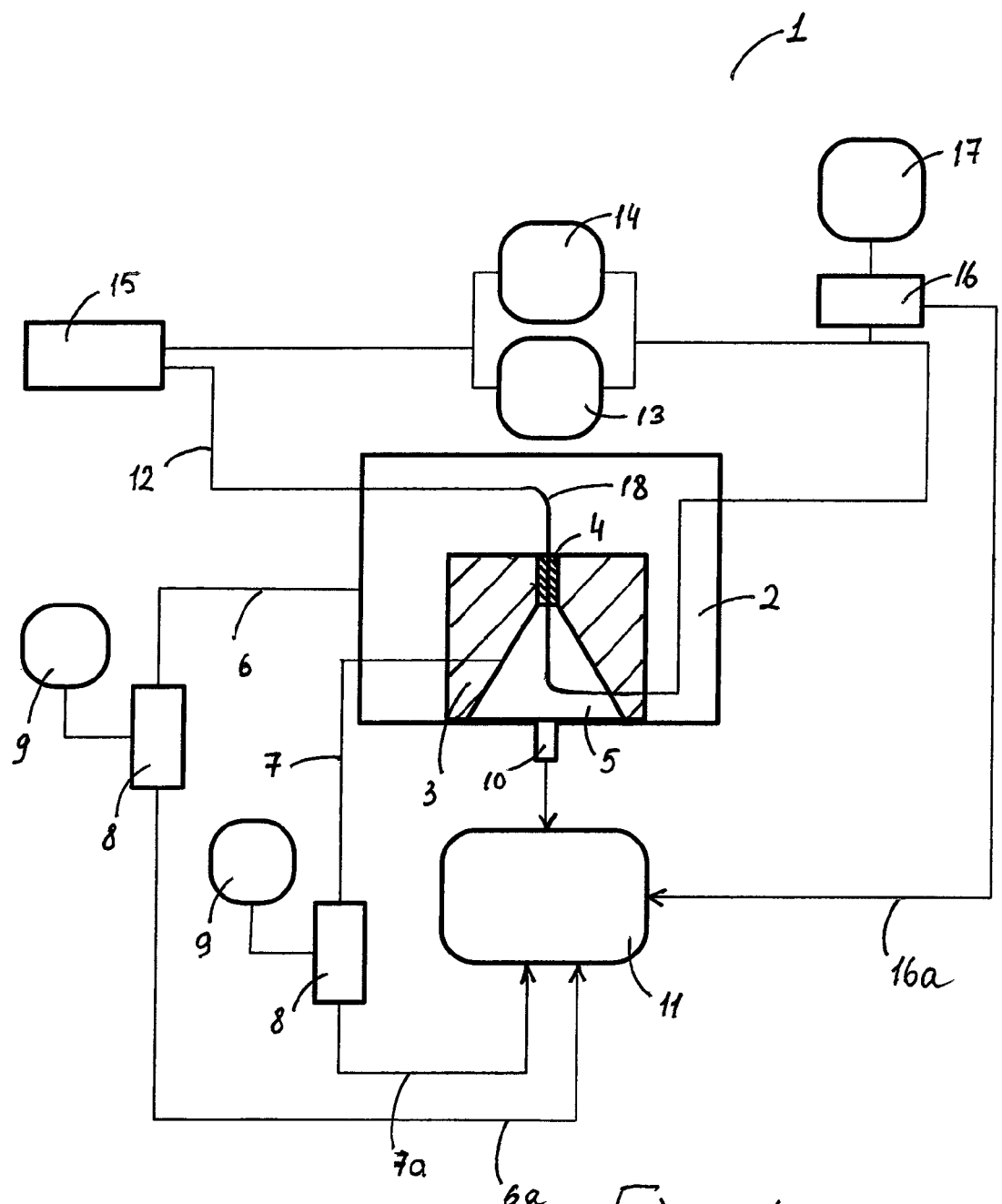
FIG. 1 is a schematic view of an apparatus for simulating arterial blood flow under various pressure conditions in accordance with the present invention.

As illustrated in FIG. 1, the device 1 consists of two chambers, a first larger chamber 2 representing the intra-cranial space, and a second smaller chamber 3 representing the orbital or extra-cranial space. In a preferred embodiment, the second chamber 3 is placed inside the first chamber 2 to more accurately simulate the orbital space located within the intra-cranial space. A tube or an artificial vessel 18 runs through both first chamber 2 and second chamber 3, simulating the course of the ophthalmic artery as it passes through an optic canal from the intra-cranial to the orbital space. A region between the two chambers, representative of an optic canal, is filled with a plug 4, which seals the first chamber 2 from the second chamber 3, and which is designed to imitate a barrier between the intra-cranial space and the orbital space. The plug 4 is preferably made with latex or silicone material, although other suitable materials known in the art may be used instead. The plug 4 provides a mechanism for mechanically joining the tube 18 and the barrier between the two chambers 2 and 3. The plug 4 is also designed to attenuate the ultrasound as little as possible.

The second chamber 3 contains a cavity 5 that is preferably conical in shape and is preferably designed such that its defining shape and volume are representative of a human orbital cavity. The portion of the orbital cavity that would be the surface of the eyeball is instead an open orifice, closed only on insertion of an ultrasound transducer 10 that is tightly fitted, sealing the orbital chamber 3.

Figure 2:
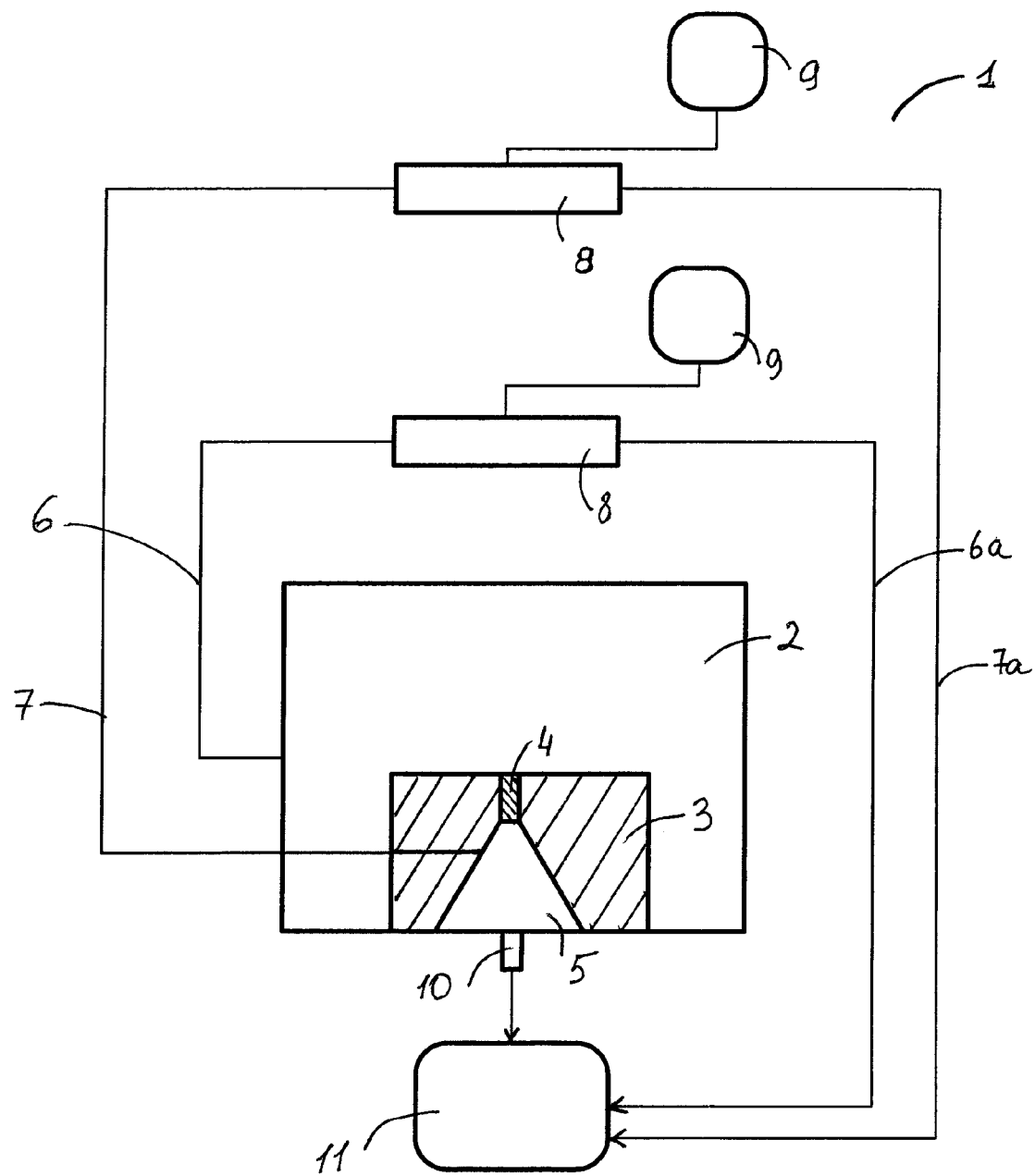
FIG. 2 is a schematic view of the apparatus of FIG. 1, showing two pressure loops.

Each of the chambers 2 and 3 can be independently pressurized by using at least two pressure loops. As illustrated in FIG. 2, a first pressure loop 6 is connected to the first chamber 2, and a second pressure loop 7 is connected to the second chamber 3. Each of the pressure loops 6 and 7 includes a water bag 9, a pressure sensor 8, and tubing interconnecting all of the components of the pressure loop. Tubing may comprise silicone material, or any other suitable material known in the art. The first chamber 2 and the second chamber 3 are pressurized by filling both chambers with a fluid, such as water, sealing the chambers, and then filling the water bags 9 with the fluid to independently adjust the pressure within the first chamber 2 and the second chamber 3. The pressure sensors 8 are also electrically connected 6a, 7a to a processor 11 to measure and record pressure within each chamber. It should be appreciated that while the example identified in this application utilizes water bags to adjust the pressure within the chambers, it is envisioned that any other device known in the art that is suitable for adjusting pressure may be utilized instead.

The lumen of the tube 18 can also be pressurized, simulating an arterial pressure. The tube 18 is made with a material designed to simulate an arterial wall, and its compliance and diameter are key in the operation of the phantom device of the present invention. Preferably, the tube 18 is made with latex material. However, any other material known in the art that is responsive to pressure changes may be used without departing from the spirit of the present invention.

Figure 3:
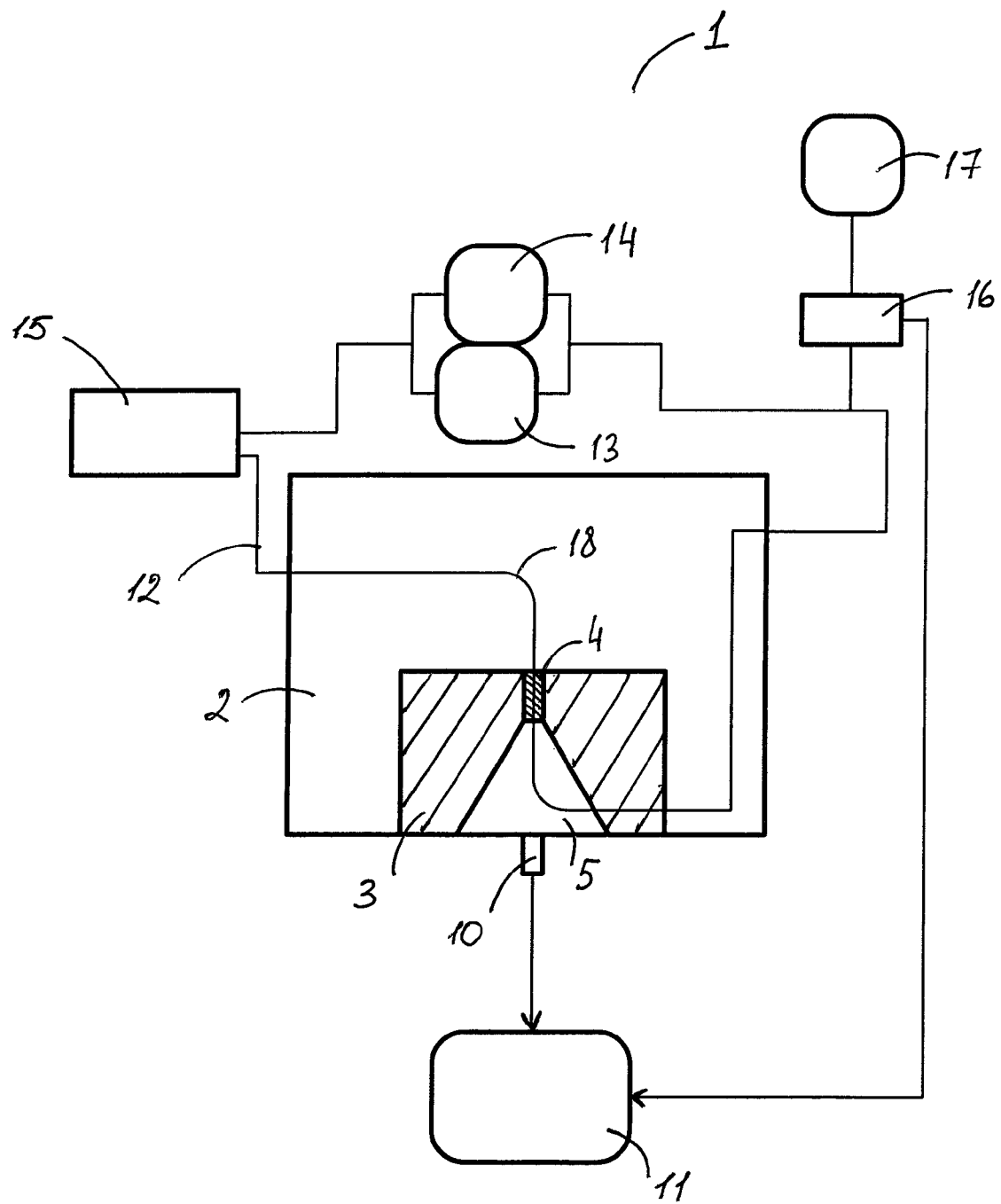
FIG. 3 is a schematic view of the apparatus of FIG. 1, showing a flow loop.

The apparatus of the present invention further comprises a flow loop 12 for controlling a fluid flow and pressure within the tube 18. A schematic view of the flow loop 12 is shown in FIG. 3. The flow loop 12 includes a flow reservoir 15, at least one constant-flow pump 13, at least one pulsatile-flow pump 14, and a pressure line 16, 17 interconnected by tubing. The flow loop 12 is connected to the tube 18 running through the first chamber 2, the second chamber 3, and the sealing plug 4 placed between the two chambers. In an exemplary embodiment of the present invention, the pressure line includes a water bag 17 and a pressure sensor 16. The water bag 17 is used to adjust/change pressure within the flow loop 12 and the tube 18. However, it should be understood that any other known device that is suitable for varying pressure within the flow loop may be used instead. The pressure sensor 16 is electrically connected 16a to the processor 11 for measuring and recording the pressure within the flow loop 12 and the tube 14. Once the flow loop 12 is assembled, the water bag 17 is preferably filled with blood simulating fluid, and the constant-flow pump 13 and the pulsatile-flow pump 14 are used to pump fluid through the tube 18 to simulate the blood flow in the human ophthalmic artery. It is possible to use only the constant-flow pump 13 or only the pulsatile-flow pump 14 to pump the fluid through the flow loop 12.

The constant-flow pump 13 and the pulsatile-flow pump 14 are placed on a surface isolated from the rest of the device in order to prevent transfer of mechanical vibrations from the pumps. The pumps 13 and 14 are connected in parallel so that they can be run separately or simultaneously without reconnecting tubing. On the outflow side of the pumps 13 and 14 latex tubing (not shown) may be placed in line to help absorb mechanical vibration from the pump as well as help shape the diastolic component of the pulsatile wave. Alternatively, a pulse dampener (not shown) may also be placed in line for the same purpose as described above.

The device is operated by independently pressurizing the first chamber 2 by using the first pressure loop 6 and the second chamber 3 by using the second pressure loop 7, and by pumping the blood simulating fluid through the tube 18 in a pulsatile manner. An ultrasound beam from the ultrasound transducer 10 that is tightly fitted into the conical cavity 5 of the second chamber 3 is then turned on, and the flow of blood simulating fluid in the intra-cranial space (the first chamber 2) and the orbital space (the second chamber 3) is visualized in the form of two spectrograms. The points at which the flow is interrogated are thus specialy distinct, both in terms of depth (distance from the transducer 10), and lateral location. The ultrasound transducer 10 is connected to the processor 11, which receives and processes the signal from the ultrasound transducer 10.

In the exemplary embodiment of the present invention, water columns are used to individually pressurize the two chambers 2 and 3 of the device. The height-pressure relationship is preferably as follows: 1.36 cm $H_{20}$=1 mmHg. Once the pressure loops are assembled and filled with water, pressure is changed by raising or lowering the water bags 9 in relation to the device. The water lines provided are preferably 200 cm in length, which will allow for over 140 mmHg.

Pressure within the first pressure loop 6 and the second pressure loop 7, as well as in the flow loop 12 may be measured by any known type of blood pressure sensor that is placed in the pressure loop and the flow loop lines. The voltage signal from the pressure sensors 8 and 16 representative of the pressure measurement is transmitted to the processor 11 via electrical lines 6a and 7a. This voltage signal may then be converted to a digital signal and the digitized signal may be sent to a host computer (not shown) which converts the digitized signal to a pressure measurement.

The above description is for the purpose of teaching the person of ordinary skill in the art how to practice the present invention, and it is not intended to detail all of those obvious modifications and variations of it which will become apparent to the skilled worker upon reading the description. It is intended however, that all such obvious modifications and variations be included within the scope of the present invention which is defined by the following claims.

What is claimed is:

1. An apparatus for simulating arterial blood flow under various pressure conditions, comprising:
    a first chamber;
    a second chamber;
    a sealing plug between said two chambers;
    a tube extending through said sealing plug from said first chamber to said second chamber;
    two pressure loops, one connected to said first chamber and the other connected to said second chamber, for independent pressurizing of each said chamber; and
    a flow loop connected to said tube for controlling a fluid flow and pressure in said tube.

2. The apparatus of claim 1, wherein said flow loop comprises a flow reservoir, at least one pump, and a pressure line.

3. The apparatus of claim 1, wherein said tube comprises material designed to simulate an arterial wall.

4. The apparatus of claim 1, wherein each of said two pressure loops is filled with a fluid.

5. The apparatus of claim 1, wherein said sealing plug comprises silicone.

6. The apparatus of claim 2, wherein said at least one pump is a pulsatile-flow pump.

7. The apparatus of claim 2, wherein said at least one pump is a constant-flow pump.

8. The apparatus of claim 2, wherein said flow loop comprises both a constant-flow pump and a pulsatile-flow pump.

9. The apparatus of claim 8, wherein said constant-flow pump and said pulsatile-flow pump are placed on an isolated surface to prevent transfer of mechanical vibrations.

10. The apparatus of claim 8, wherein said constant-flow pump and said pulsatile-flow pump are connected in parallel.

11. The apparatus of claim 8, further comprising tubing placed on an outflow side of said constant-flow pump and said pulsatile-flow pump to assist with absorption of mechanical vibration from said pumps.

12. The apparatus of claim 8, further comprising a pulse dampener placed on an outflow side of said constant-flow pump and said pulsatile-flow pump to assist with absorption of mechanical vibration from said pumps.

13. The apparatus of claim 2, wherein said pressure line comprises a water bag and a pressure sensor.

14. The apparatus of claim 13, wherein said pressure sensor is connected to a processor.

15. The apparatus of claim 13, wherein said water bag is filled with a blood simulating fluid.

16. The apparatus of claim 15, wherein said blood simulating fluid is pumped through said flow loop in a pulsatile manner.

17. The apparatus of claim 1, wherein said second chamber comprises a cavity that is conical in shape to simulate an orbital cavity.

18. The apparatus of claim 17, further comprising an ultrasound transducer fitted into said cavity thereby sealing said second chamber.

19. The apparatus of claim 1, wherein each of said two pressure loops comprises a pressure sensor and a water bag.

20. The apparatus of claim 19, wherein said sensor is connected to a processor.

21. An apparatus for simulating arterial blood flow under various pressure conditions, comprising:
    a first chamber;
    a second chamber;
    a sealing plug between said two chambers;
    a tube extending through said sealing plug from said first chamber to said second chamber, said tube connected to a flow loop comprising a flow reservoir, a constant-flow pump, a pulsatile-flow pump, and a pressure line for controlling a fluid flow and pressure in said tube; and
    two pressure loops, one connected to said first chamber and the other connected to said second chamber, for independent pressurizing of each said chamber;
    wherein said pressure line comprises a water bag and a pressure sensor;
    wherein a blood simulating fluid is pumped through said flow loop in a pulsatile manner; and
    wherein said two pressure loops comprise a water bag and a pressure sensor.

22. A method for simulating arterial blood flow under various pressure conditions, comprising the steps of:
    pressurizing a first chamber using a first pressure loop;
    pressurizing a second chamber using a second pressure loop;
    connecting said first chamber with said second chamber by a tube;
    connecting said tube to a flow loop; and
    pressurizing said flow loop and said tube by pumping a fluid through said tube and said flow loop.

23. The method of claim 22, wherein said fluid is pumped through said tube and said flow loop in a pulsatile manner.

24. The method of claim 22, further comprising the step of measuring a flow of the fluid in said tube using an ultrasound transducer.

25. The method of claim 22, further comprising the step of measuring pressure in said first chamber and transmitting a signal representing the pressure to a processor.

26. The method of claim 22, further comprising the step of measuring pressure in said second chamber and transmitting a signal representing the pressure to a processor.

* * * * *